United States Patent
Justis et al.

(10) Patent No.: US 8,298,270 B2
(45) Date of Patent: *Oct. 30, 2012

(54) PIVOTING JOINTS FOR SPINAL IMPLANTS INCLUDING DESIGNED RESISTANCE TO MOTION AND METHODS OF USE

(75) Inventors: Jeff R. Justis, Germantown, TN (US); Fred J. Molz, IV, Birmingham, AL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 220 days.

This patent is subject to a terminal disclaimer.

(21) Appl. No.: 12/762,869

(22) Filed: Apr. 19, 2010

(65) Prior Publication Data

US 2010/0199483 A1  Aug. 12, 2010

Related U.S. Application Data

(62) Division of application No. 11/341,188, filed on Jan. 27, 2006, now Pat. No. 7,722,652.

(51) Int. Cl.
*A61B 17/88* (2006.01)
(52) U.S. Cl. .......... 606/279; 606/264; 606/306
(58) Field of Classification Search .......... 606/279, 606/264–270, 305, 306, 308
See application file for complete search history.

(56) References Cited

U.S. PATENT DOCUMENTS

| | | | |
|---|---|---|---|
| 5,728,098 A * | 3/1998 | Sherman et al. | 606/269 |
| 6,082,923 A | 7/2000 | Maughan | |
| 6,132,434 A | 10/2000 | Sherman et al. | |
| 6,280,442 B1 * | 8/2001 | Barker et al. | 606/60 |
| 6,454,773 B1 | 9/2002 | Sherman et al. | |
| 7,559,943 B2 | 7/2009 | Mujwid | |
| 7,699,876 B2 | 4/2010 | Barry et al. | |
| 7,833,252 B2 * | 11/2010 | Justis et al. | 606/279 |
| 2005/0080415 A1 * | 4/2005 | Keyer et al. | 606/61 |
| 2005/0277919 A1 * | 12/2005 | Slivka et al. | 606/61 |
| 2006/0276792 A1 * | 12/2006 | Ensign et al. | 606/61 |
| 2008/0147121 A1 | 6/2008 | Justis et al. | |

* cited by examiner

*Primary Examiner* — Ellen C Hammond (57) ABSTRACT

Methods of assembling a vertebral anchor to a body shaped to receive a longitudinal member. The methods may include inserting a wear member and a head of an anchor into a cavity through an inlet in a first end of a body. The body may further include a second end with a channel to receive the longitudinal member. The method may include deforming the first end of the body and reducing a width of the inlet measured perpendicular to a longitudinal axis of the body and capturing the wear member and the head in the cavity. The method may also include compressing the wear member against the head of the anchor and increasing an amount of interference between the wear member and the head.

13 Claims, 11 Drawing Sheets

PIVOTING JOINTS FOR SPINAL IMPLANTS INCLUDING DESIGNED RESISTANCE TO MOTION AND METHODS OF USE

RELATED APPLICATION

The present application is a divisional application of U.S. patent application Ser. No. 11/341,188 filed on Jan. 27, 2006, now U.S. Pat. No. 7,722,652, and herein incorporated by reference in its entirety.

BACKGROUND

Longitudinal members, such as spinal rods, are often used in the surgical treatment of spinal disorders such as degenerative disc disease, disc herniations, scoliosis or other curvature abnormalities, and fractures. Different types of surgical treatments are used. In some cases, spinal fusion is indicated to inhibit relative motion between vertebral bodies. In other cases, dynamic implants are used to preserve motion between vertebral bodies. For either type of surgical treatment, longitudinal members may be attached to the exterior of two or more vertebrae, whether it is at a posterior, anterior, or lateral side of the vertebrae. In other embodiments, longitudinal members are attached to the vertebrae without the use of dynamic implants or spinal fusion.

Longitudinal members may provide a stable, rigid column that encourages bones to fuse after spinal-fusion surgery. Further, the longitudinal members may redirect stresses over a wider area away from a damaged or defective region. Also, rigid longitudinal members may restore the spine to its proper alignment. In some cases, flexible longitudinal members may be appropriate. Flexible longitudinal members may provide other advantages, such as increasing loading on interbody constructs, decreasing stress transfer to adjacent vertebral elements while bone-graft healing takes place, and generally balancing strength with flexibility.

Conventionally, longitudinal members are secured to vertebral members using rigid clamping devices. These clamping devices may be multi-axial in the sense that they are adjustable prior to securing. However, once secured, the clamping devices are locked in place. A surgeon may wish to implant a flexible rod system and have more freedom to control pivot points or the nature of the pivoting motion. At present, a surgeon might only have a choice between rigid and flexible longitudinal members, which may not necessarily provide the desired degree of flexibility.

SUMMARY

The present application is directed to methods of assembling a vertebral anchor to a body shaped to receive a longitudinal member. The methods may include inserting a wear member and a head of an anchor into a cavity through an inlet in a first end of a body. The body may further include a second end with a channel to receive the longitudinal member. The method may include deforming the first end of the body and reducing a width of the inlet measured perpendicular to a longitudinal axis of the body and capturing the wear member and the head in the cavity. The method may also include compressing the wear member against the head of the anchor and increasing an amount of interference between the wear member and the head.

DETAILED DESCRIPTION

Figure 1A:
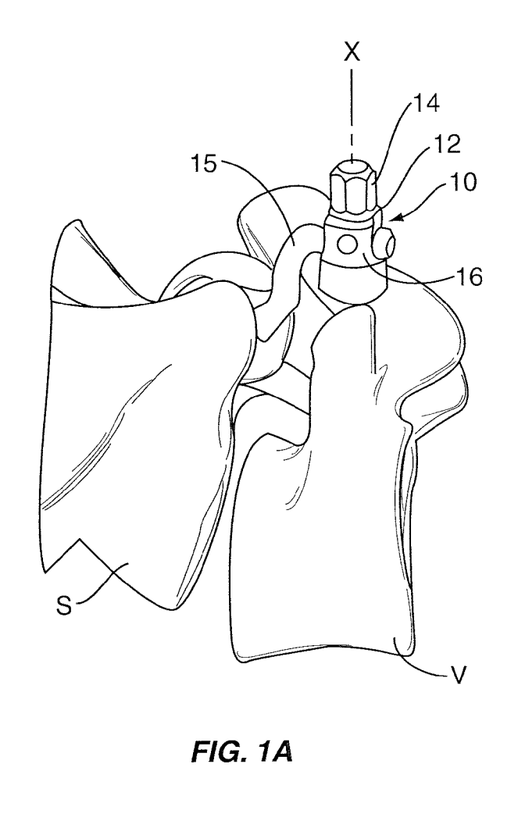
FIGS. 1A and 1B are perspective views of a pivoting head assembly according to one or more embodiments comprising a longitudinal member attached to the spine.
Figure 1B:
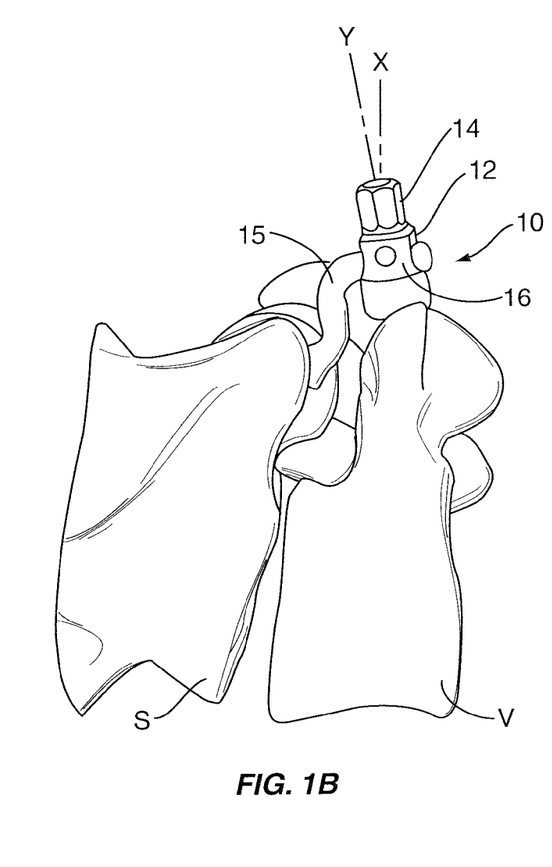

The various embodiments disclosed herein are directed to pivoting mechanisms and methods for securing longitudinal members in a spinal implant. Various types of longitudinal members are contemplated, including spinal rods that may be secured between multiple vertebral bodies. FIGS. 1A and 1B show another type of longitudinal member 15 that is secured between the sacrum S and a vertebral member V (i.e., L5). In one embodiment, the longitudinal member 15 is a flexible member, such as a resin or polymer compound. Some flexible non-metallic longitudinal members 15 are constructed from materials such as PEEK and UHMWPE. Other types of flexible longitudinal members 15 may comprise braided metallic structures. In one embodiment, the longitudinal member 15 is rigid or semi-rigid and may be constructed from metals, including for example stainless steels, cobalt-chrome, titanium, and shape memory alloys. Further, the longitudinal member 15 may be straight, curved, or comprise one or more curved portions along its length.

In FIGS. 1A and 1B, the longitudinal member 15 is secured to the vertebral member V with one embodiment of a pivoting head 10 in accordance with the teachings provided herein. In the embodiment shown, the longitudinal member 15 is secured to a saddle 16 within the pivoting head 10 with a securing member 12. The securing member 12 shown in FIGS. 1A and 1B features a snap-off driving member 14. The driving member 14 is integrally formed with the securing member 12 and allows a surgeon to drive the securing member 12 into contact with the longitudinal member 15 to achieve a certain installation torque. Above that torque, the driving member 14 will snap off, separating from the securing member 12. In this manner, the securing member 12 may provide the desired clamping force to secure the longitudinal member 15.

FIG. 1A shows a first orientation for the pivoting head 10 identified by the centerline labeled X. By contrast, FIG. 1B shows a second position representing a different spatial relationship between the sacrum S and the vertebra V. As compared to FIG. 1A, the vertebra V in FIG. 1B exhibits some amount of angular and torsional displacement relative to the sacrum S. Consequently, the pivoting head 10 is illustrated in a second orientation identified by the centerline labeled Y. The pivoting head 10 may provide some or all of this rotation. The illustrations provided in FIGS. 1A and 1B show the pivoting head 10 as part of a spinal implant that is coupled between a vertebral body V and a sacrum S. It should be understood that the pivoting head 10 may be used in constructs that are coupled to vertebral bodies V alone. Further, a vertebral implant may be construed to mean implants that are coupled to any or all portions of a spine, including the sacrum, vertebral bodies, and the skull.

Figure 2A:
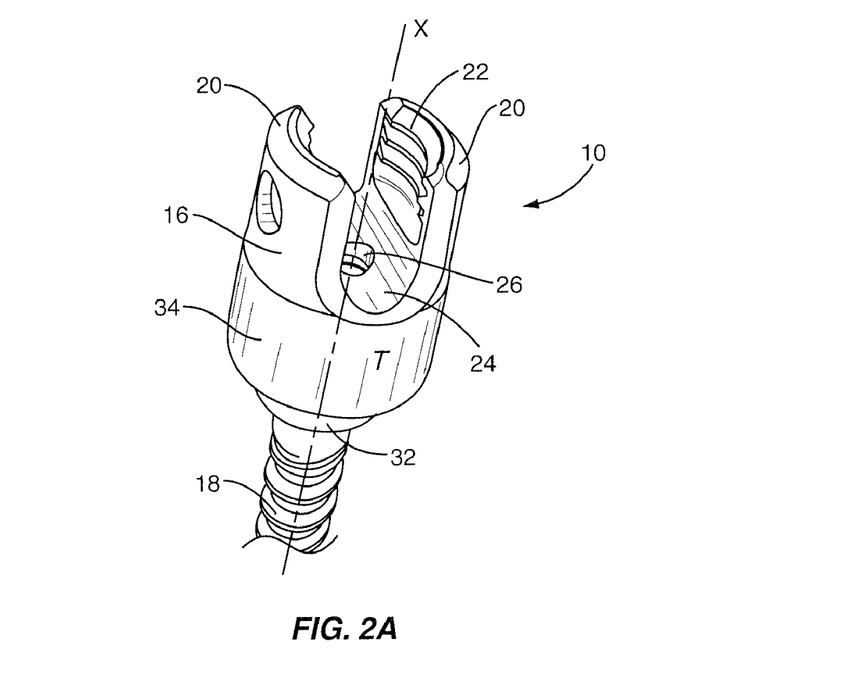
FIGS. 2A and 2B are perspective views of a pivoting head coupled to an anchor member according to one embodiment.
Figure 2B:
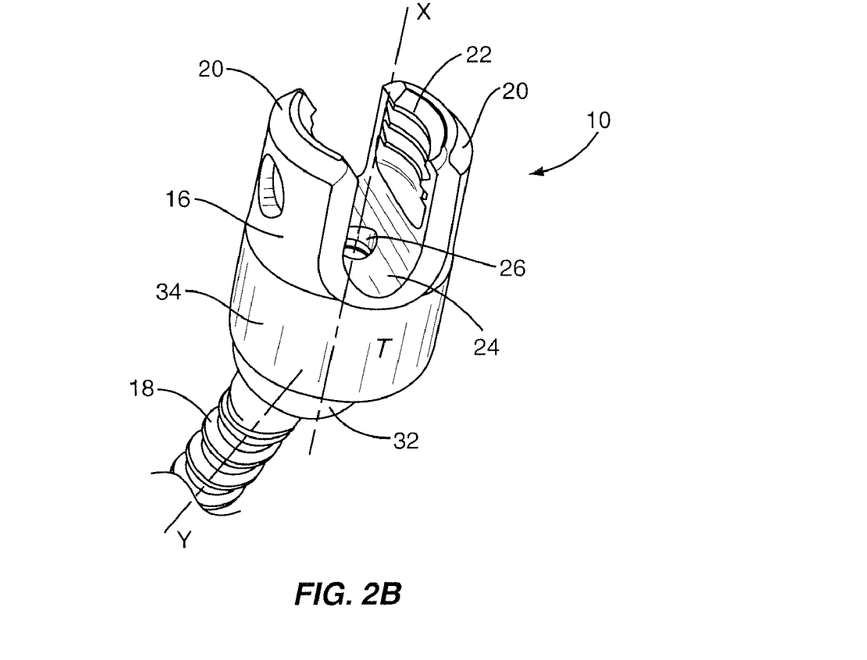

FIGS. 2A and 2B illustrate perspective views of the illustrative embodiment of the pivoting head 10 coupled to an anchor member 18. A head 32 of the anchor member 18 is pivotally coupled to a base portion 34 of the pivoting head 10. In one embodiment, the anchor member 18 comprises threads for insertion into a vertebral member V as shown in FIGS. 1A and 1B. In one embodiment, the anchor member 18 is a pedicle screw. The exemplary saddle 16 is comprised of opposed upright portions forming a U-shaped channel within which a longitudinal member 15 is placed. A seating surface 24 forms the bottom of the U-shaped channel. In one embodiment, the seating surface 24 is curved to substantially match the radius of a longitudinal member 15 that is positioned within the saddle 16. An aperture 26 within the seating surface provides access to a driving feature used to insert the anchor member 18 into a vertebral member V.

In FIG. 2A, the pivoting head 10 is shown substantially aligned with the anchor member 18 along the centerline labeled X. In FIG. 2B, the anchor member 18 is shown pivoted relative to the pivoting head 10. That is, the pivoting head 10 is shown still aligned with the centerline labeled X while the anchor member 18 is shown aligned with the centerline labeled Y. The pivoted displacement of the pivoting head 10 relative to the anchor member 18 achieved in FIG. 2B is provided by an articulation mechanism that is more clearly visible in the section view provided in FIG. 3.

Figure 3:
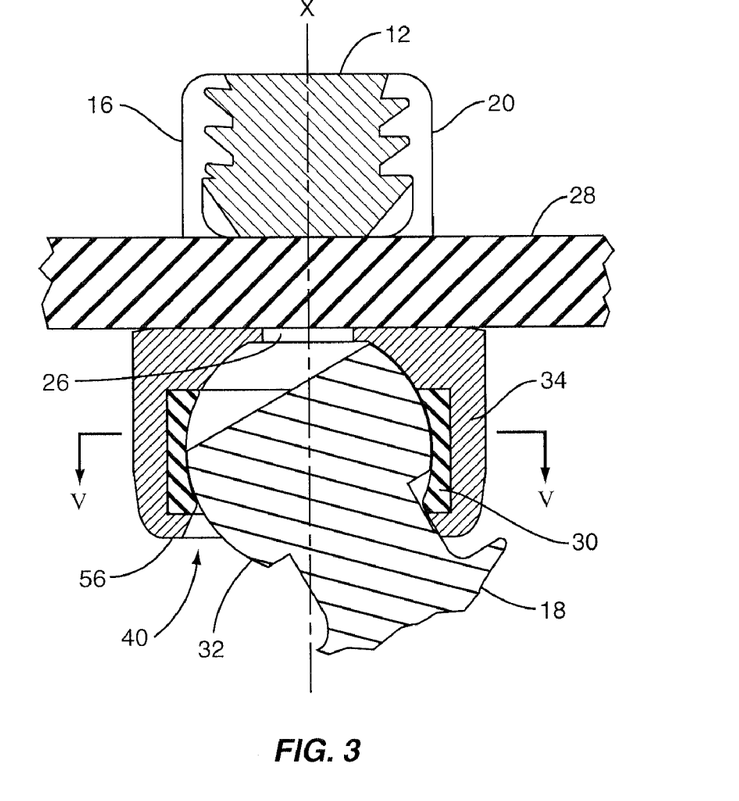
FIG. 3 is a side section view of a pivoting head coupled to an anchor member and securing a longitudinal member according to one embodiment.

FIG. 3 shows a section view of the pivoting head 10 holding a different type of longitudinal member 28. In this embodiment, the longitudinal member 28 is a spinal rod. The spinal rod 28 is secured within the saddle 16 with a securing member 12. In the embodiment shown, the securing member 12 is an externally threaded set screw, though other types of securing members such as externally threaded caps and nuts may be used. In the embodiment shown, an articulation mechanism 40 is disposed below the saddle 16 and generally aligned with the central axis X. The articulation mechanism 40 comprises an anchor head 32 of the anchor member 18 that is pivotally coupled to a wear member 30 within the base portion 34 of the pivoting head 10. Since the anchor head 32 is configured to pivot within the wear member 30, the wear member 30 and the outer surface of the anchor head 32 may be constructed of a wear resistance material. Some suitable examples may include hardened metals, titanium carbide, cobalt chrome, polymers, and ceramics.

In other embodiments, a wear resistant layer may be coated onto the anchor head 32 and the wear member 30. In one embodiment, the wear member 30 may be integrally formed into or form a part of the base portion 34. In one embodiment, the wear member 30 may be bonded to the base portion 34 using a biocompatible adhesive such as PMMA or other known adhesives. In these alternative embodiments, the part of the base portion 34 in contact with the anchor head 32 may be coated with a wear resistant layer. Coating processes that include, for example, vapor deposition, dip coating, diffusion bonding, and electron beam welding may be used to coat the above indicated materials onto a similar or dissimilar substrate. Diffusion bonding is a solid-state joining process capable of joining a wide range of metal and ceramic combinations. The process may be applied over a variety of durations, applied pressure, bonding temperature, and method of heat application. The bonding is typically formed in the solid phase and may be carried out in vacuum or a protective atmosphere, with heat being applied by radiant, induction, direct or indirect resistance heating. Electron beam welding is a fusion welding process in which a beam of high-velocity electrons is applied to the materials being joined. The workpieces melt as the kinetic energy of the electrons is transformed into heat upon impact. Pressure is not necessarily applied, though the welding is often done in a vacuum to prevent the dispersion of the electron beam.

The articulation mechanism 40 is spatially and functionally isolated from the clamping forces that are applied between the securing member 12, the rod 28, and the seating surface 24 (see FIGS. 2A, 2B). That is, since the compression forces applied by the securing member 12 are not transmitted to the articulation mechanism 40, the anchor member 18 rotates about the central axis X under the influence of the sliding resistance provided by the various embodiments disclosed herein. In this manner, the articulation mechanism 40 is not only spatially isolated from the securing member 12, but also physically isolated from the forces provided by the securing member 12.

Figure 4:
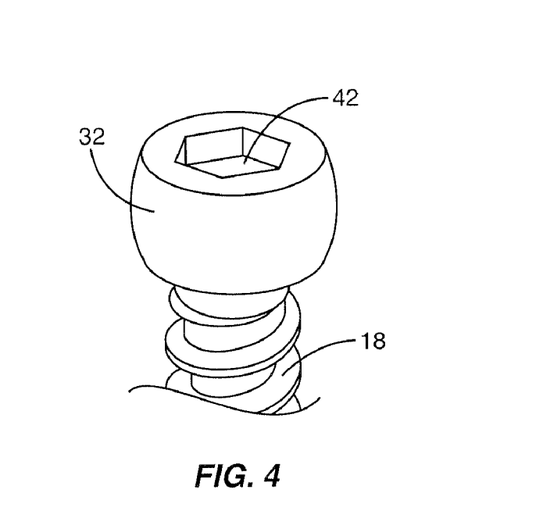
FIG. 4 is a perspective view of an anchor member for use with a pivoting head according to one embodiment.

FIG. 4 shows a perspective view of the anchor head 32 of the exemplary anchor member 18. The anchor head 32 includes a driving feature 42 that allows a surgeon to attach the anchor member 18 to a vertebra V. In the embodiment shown, a hex recess driving feature 42 is shown. Other types of driving features 42 may be appropriate, including for example, slotted, star, Torx, and cross-shaped features. The driving feature 42 may be accessed through the aperture 26 shown in FIGS. 2A, 2B, and 3.

Figure 5A:
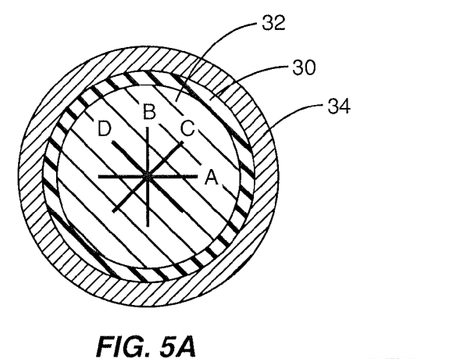
FIGS. 5A-C are top section views of a pivoting head with an anchor member and wear member inserted therein according to different embodiments.
Figure 5B:
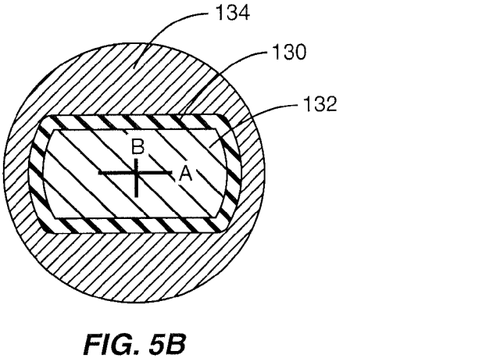
Figure 5C:
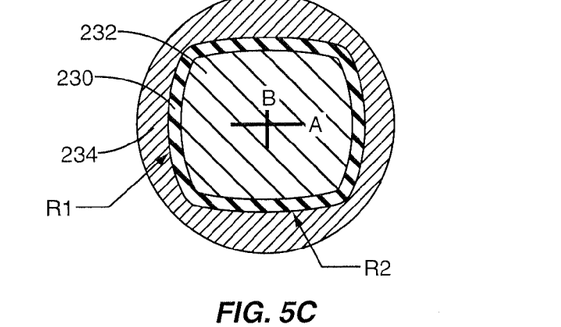

In the embodiment illustrated in FIG. 4, the anchor head 32 is substantially spherical to allow multi-axial pivoting of the anchor member 18 relative to the pivoting head 10. In other embodiments, the anchor head 32 has other shapes to allow motion in fewer directions. For instance, a disc-shaped anchor head 32 may provide motion within a desired plane. FIGS. 5A, 5B, and 5C illustrate some of these alternative embodiments. Specifically, FIGS. 5A-5C are top section views according to the section line X-X shown in FIG. 3. FIG. 5A shows one embodiment where the anchor head 32 and wear member 30 are substantially spherical as previously described. With this configuration, the pivoting head 10 may pivot about a plurality of axes, including axes A, B, C, and D as shown in FIG. 5A. FIG. 5B shows an alternative embodiment where the anchor head 132 and wear member 130 are substantially disc-shaped. As disclosed above, this configuration may allow pivoting motion about axis B, but not other axes, including axis A. FIG. 5C depicts another embodiment that is characterized by at least two different spherical radii R1, R2. This configuration may provide a different resistance to rotation about axes A and B. A somewhat pronounced difference in radii R1, R2 is shown in FIG. 5C, though in practice, a fairly small difference may produce the desired result.

Figure 6:
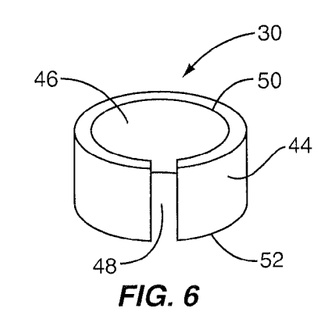
FIG. 6 is a perspective view of a wear member for use with a pivoting head according to one embodiment.

FIG. 6 shows a perspective view of a wear member 30 according to one embodiment. As depicted, the wear member 30 is cylindrically shaped and includes an outer surface 44 and an inner surface 46 extending between a top surface 50 and a bottom surface 52. Generally, the inner surface 46 is constructed to match the shape of the anchor head 32 of the threaded anchor member 18. The outer surface 44 may be configured as desired to fit within the base portion 34 of the pivoting head 10 as shown in FIG. 3. In one embodiment, the outer surface 44 is substantially cylindrical. The exemplary wear member 30 also includes a gap 48. The gap 48 in the present embodiment may be used to spread open the wear member 30 by an amount sufficient to slip the wear member 30 over the anchor head 32 of the anchor member 18.

Figure 7:
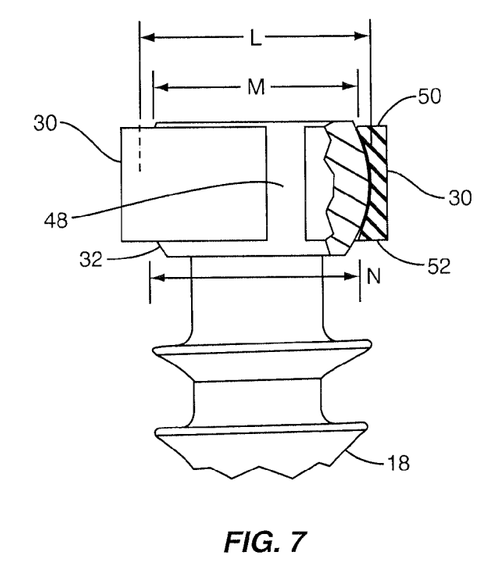
FIG. 7 is a side view, including a partial section view, of an assembled anchor member and wear member for use with a pivoting head according to one embodiment.

The wear member 30 is shown installed on the anchor head 32 in FIG. 7. FIG. 7 also shows relevant dimensions of the wear member 30 and the anchor head 32. Dimension L represents a width of the anchor head 32 at its widest point. The width may comprise a diameter, a spherical diameter, or other linear dimension. Dimensions M and N respectively represent an interior width at the top 50 and bottom 52 of the wear member 30. Notably, dimension L is larger than both M and N. Thus, the gap 48 allows the anchor head 32 to fit within the wear member 30 as shown in FIG. 7.

Figure 8:
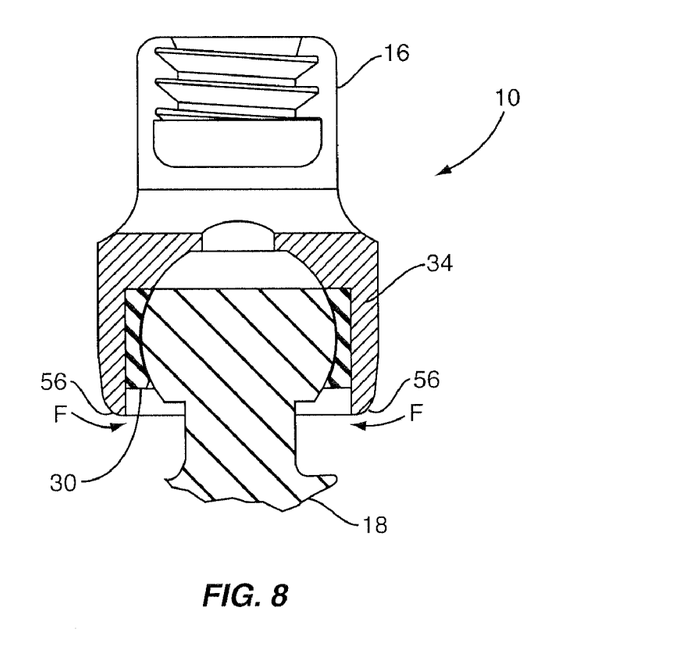
FIG. 8 is a side section view of a pivoting head with an anchor member and wear member inserted therein according to one embodiment.
Figure 9:
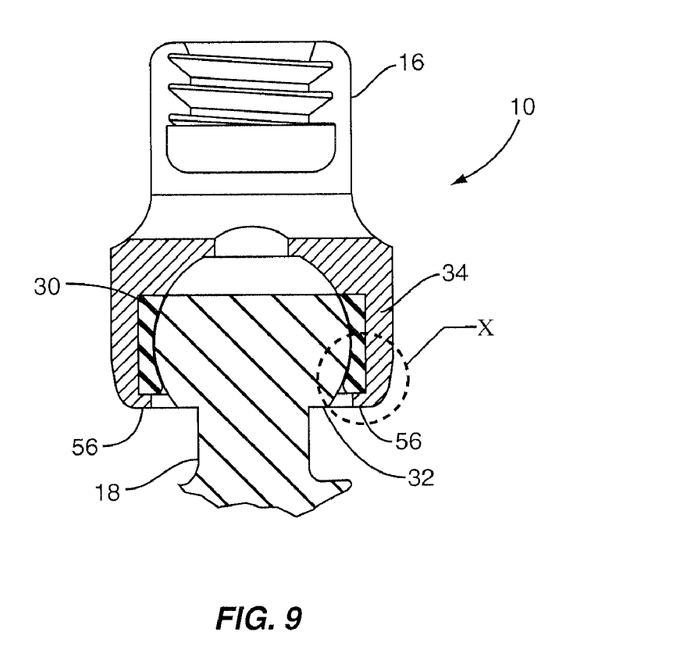
FIG. 9 is a side section view of an assembled pivoting head with an anchor member and wear member constrained therein according to one embodiment.

FIG. 8 shows the assembled wear member 30 and anchor member 18 inserted into the base portion 34 of the pivoting head 10. The anchor member 18 and wear member 30 are retained within the base portion 34 by deforming the lower lip 56 in the direction of the arrow labeled F. The deforming step may be performed using a variety of techniques, including but not limited to mechanical pressing, swaging, and orbital forming. Orbital forming (or orbital forging) is a cold metal forming process during which the workpiece (the base portion 34 in this case) is transformed between upper and lower dies. The process features one or the other of these dies orbiting relative to the other with a compression force applied therebetween. Due to this orbiting motion over the workpiece, the resultant localized forces can achieve a high degree of deformation at a relatively low compression force level. The fully assembled pivoting head 10 is illustrated in FIG. 9. In this Figure, the lower lip 56 of the base portion 34 is formed to constrain the wear member 30 and the anchor member 18.

Figure 10:
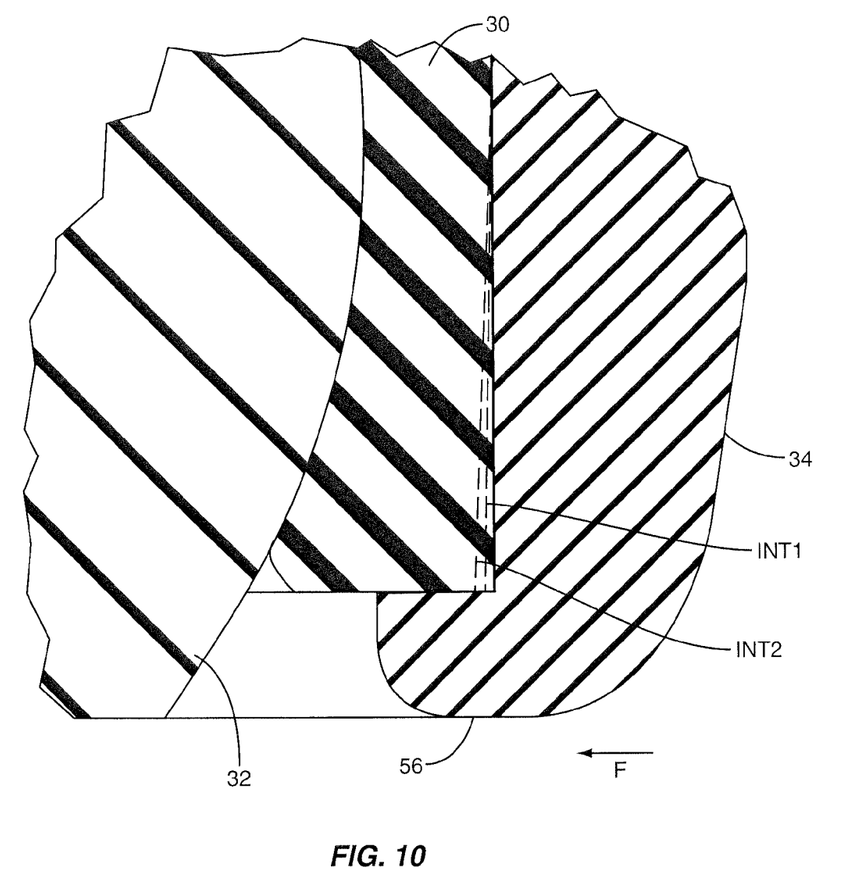
FIG. 10 is a detailed section view of the bottom region of a pivoting head according to one embodiment.

FIG. 10 shows a detail view of the lower lip 56 of the base portion 34. The forming technique used to form the lower lip 56 under and around the wear member 30 may be controlled to produce a pivoting head 10 with a desired, predetermined resistance to motion. The dashed lines labeled INT1 and INT2 depict this ability to control the amount of interference between the parts, and hence the amount of resistance to motion. If a greater amount of resistance to motion is desired, the lower lip 56 may be deformed a greater amount as indicated by the dashed line labeled INT2. A lesser amount of deformation indicated by the dashed line INT1 may produce less resistance to motion. In one embodiment, the lower lip 56 is formed to produce a very large resistance to motion such that the pivoting head 10 is, for all practical purposes, fixed. At the opposite end of the spectrum, the lower lip 56 is formed to merely place the relevant parts (base portion 34, wear member 30, and anchor head 32) in contact with one another or in close proximity to one another. In this embodiment, the pivoting head 10 is free to rotate with very little or no resistance to motion. At points between these extremes (indicated by dashed line INT1), a desired amount of interference may produce a desirable resistance to motion.

The resistance to motion may be measured in standard torque units, such as inch-ounces or other units of measure. As the parts are formed, the measurable resistance to motion may be marked on the exterior of the pivoting head 10 to provide surgeons an indication of the relative flexibility of the pivoting head 10. This marking may be provided as an alpha-numeric indication as represented by the letter T in FIGS. 2A and 2B. The marking may be stamped, whether by ink or metal deformation, engraved, or otherwise displayed on the pivoting head 10.

Figure 11:
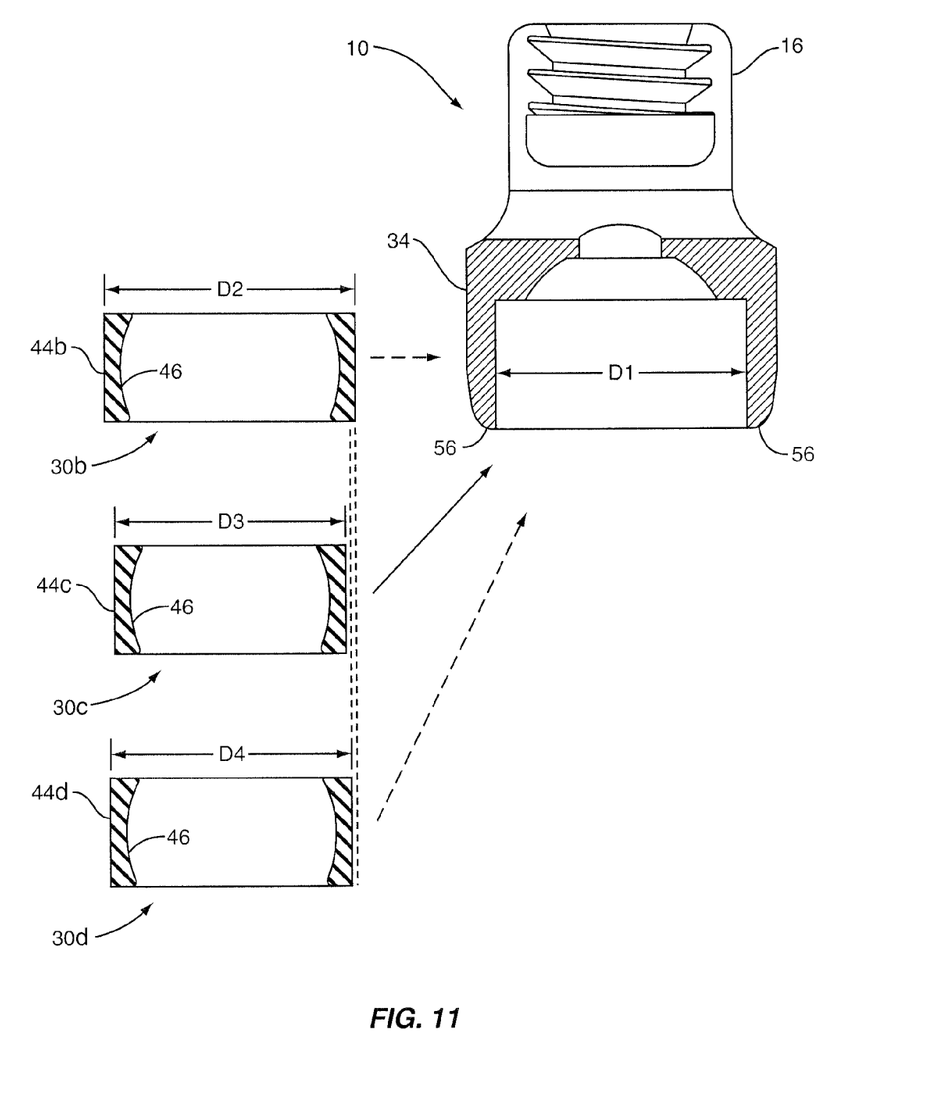
FIG. 11 is a side section view of a pivoting head and various wear members that may be used with the pivoting head according to one embodiment.

Interference between the base portion 34, the wear member 30, and the anchor head 32 will generally contribute to greater amounts of resistance to motion. Accordingly, the parts may be selected according to size to provide the desired resistance to motion. For instance, FIG. 11 shows a pivoting head 10, including a base portion 34 that is defined in part by a dimension D1. This dimension D1 corresponds approximately to the outer dimension of the wear members 30b, 30c, and 30d that are also shown in FIG. 10. However, each wear member 30b-d has a slightly different outer dimension D2-D4. As an example, wear member 30b is characterized by the largest outer dimension D2. Wear member 30c is characterized by the smallest outer diameter D3 and wear member 30d is somewhere between, with an outer diameter D4. It is assumed for the sake of this discussion, that the inner surface 46 is the same for all three wear members 30b-d. In an alternative embodiment, the inner surface 46 may be constructed with different sizes to create different amounts of interference with the anchor head 32 of the anchor member 18. In an alternative embodiment, both the inner 46 and outer 44 surfaces may vary between wear members 30. That is, different wear members 30 may have different thicknesses. In an alternative embodiment, the resistance to pivoting motion of the head 32 may be provided by materials having different coefficients of friction.

For the embodiments shown in FIG. 11, wear member 30c will result in the least amount of interference when used in the pivoting head 10. Conversely, wear member 30b will result in the greatest amount of interference when used in the pivoting head 10. A measurable resistance to motion of the pivoting head 10 can be determined once the parts are assembled. As indicated above, this measured resistance to motion may be marked on the exterior of the pivoting head 10 to provide surgeons an indication of the relative flexibility of the pivoting head 10.

Figure 12:
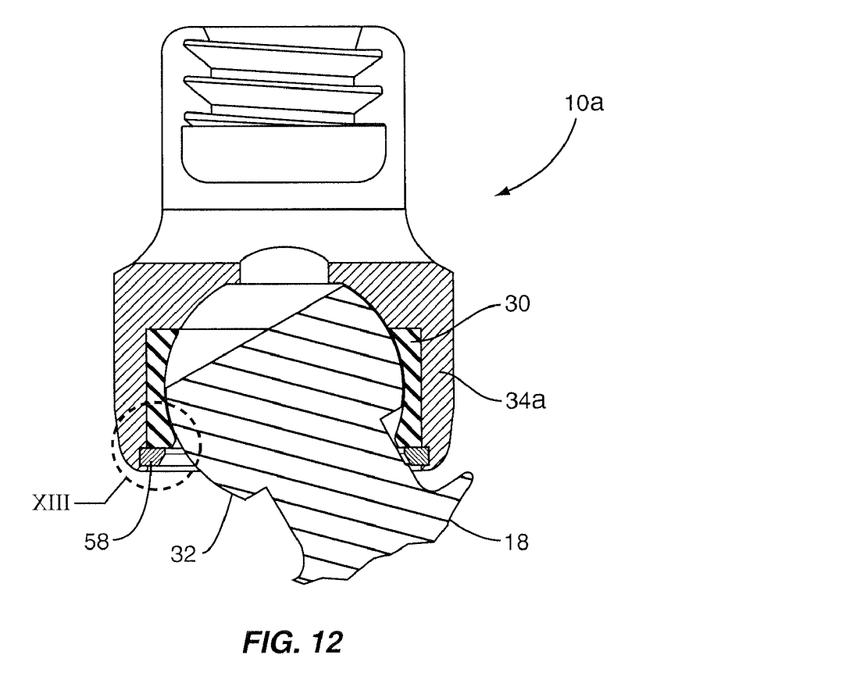
FIG. 12 is a side section view of an assembled pivoting head with an anchor member and wear member constrained therein according to one embodiment.
Figure 13:
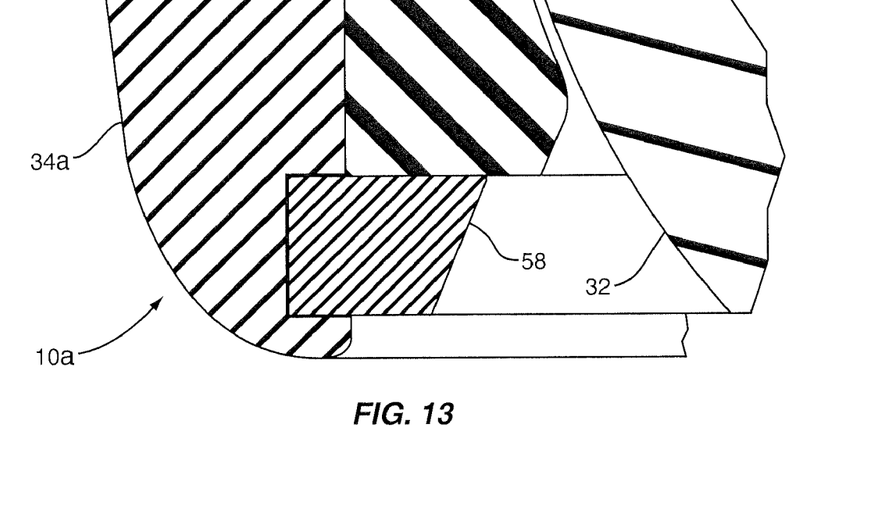
FIG. 13 is a detailed section view of the bottom region of a pivoting head according to one embodiment.

FIG. 12 shows an alternative embodiment of the pivoting head 10a. The section view shows an alternative technique for retaining the wear member 30 and anchor member 18 within the base portion 34a. In this embodiment, a snap ring 58 is inserted into the bottom of the base portion 34a beneath the wear member 30. The snap ring 58 may effectively retain the wear member 30 and anchor member 18 within the pivoting head 10a. A detailed view of the area around the snap ring 58 is shown in FIG. 13. Notably, in this embodiment, the snap ring 58 acts as a barrier to prevent the wear member 30 from escaping but does not contribute to any interference between the other parts (30, 32, 34).

Figure 14:
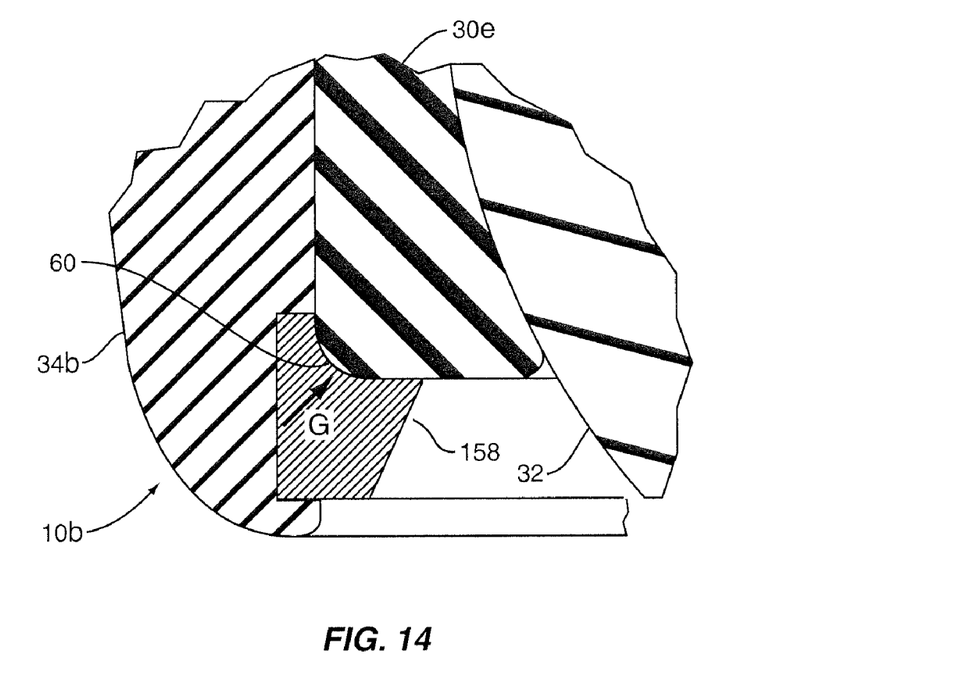
FIG. 14 is a detailed section view of the bottom region of a pivoting head according to one embodiment.
Figure 15:
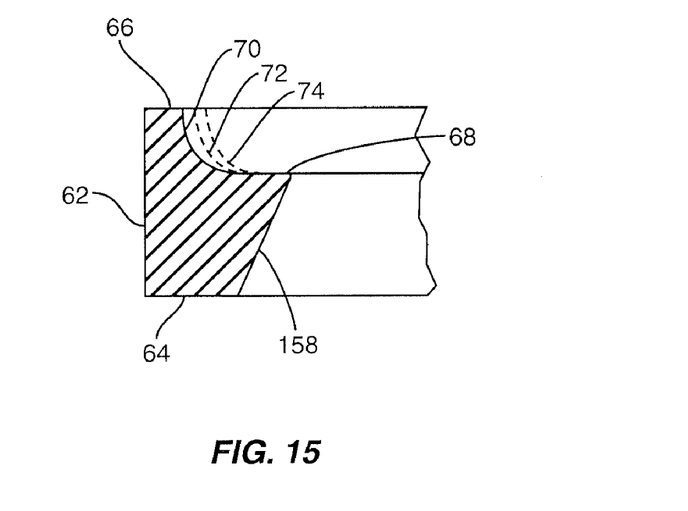
FIG. 15 is a detailed section view of an interference snap ring that may be used with the pivoting head according to one embodiment.

In an alternative embodiment shown in FIG. 14, a snap ring 158 may contribute to the overall resistance to motion of the pivoting head 10b. As with the embodiment shown in FIGS. 12 and 13, the snap ring 158 is configured to fit within the interior of the base portion 34b. However, the interior portion of the snap ring 158 is modified slightly to create an interference with the wear member 30e. In this embodiment, the wear member 30e is slightly modified to include a rounded lower outside corner 60 to facilitate insertion of the snap ring 158. A detailed view of a cross section of the snap ring 158 is shown in FIG. 15.

The exemplary snap ring 158 comprises a bottom surface 64, a top surface 66, and an outer surface 62, each of which are configured to fit within the body portion 34b of the pivoting head 10b. A retaining surface 68 further acts to keep the wear member 30e within the pivoting head 10b. This snap ring 158 also includes an interference surface 70 that contacts the wear member 30e to create a force G (shown in FIG. 14) that compresses the wear member 158 towards the anchor head 32. The compression force G creates an interference that resists pivoting motion of the anchor head 32 relative to the wear member 30e. Snap rings 158 including different interference surfaces 72, 74 may be selected to create more or less interference as desired. Once the snap ring 158 is assembled to retain and compress the wear member 30e, a measurable resistance to motion of the pivoting head 10b can be determined. As indicated above, this measured resistance to motion may be marked on the exterior of the pivoting head 10b to provide surgeons an indication of the relative flexibility of the pivoting head 10b.

Figure 16:
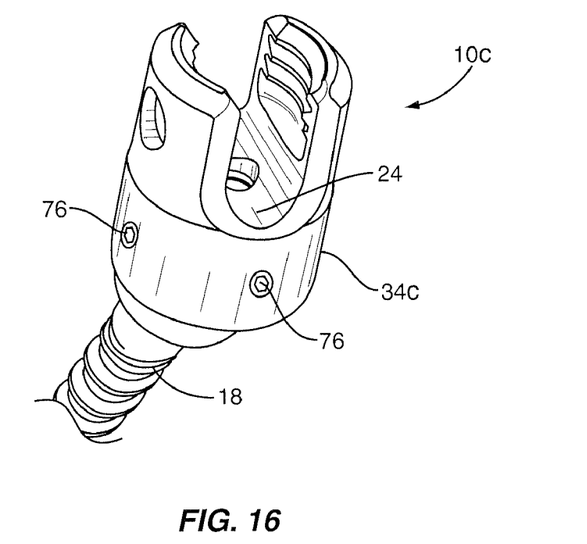
FIG. 16 is a perspective view of a pivoting head coupled to an anchor member according to one embodiment.
Figure 17:
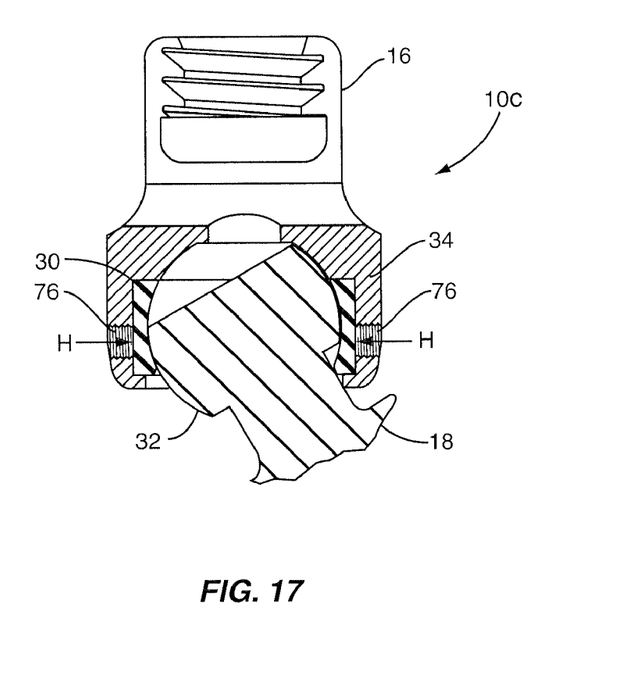
FIG. 17 is a side section view of an assembled pivoting head with an anchor member and wear member constrained therein according to one embodiment.

FIGS. 16 and 17 illustrate an alternative embodiment of the pivoting head 10c. In this embodiment, the resistance to motion may be set intra-operatively. The base portion 34c of the pivoting head 10c includes one or more adjustment members 76 that allow a surgeon to adjust the amount of interference between the wear member 30 and the anchor head 32. Further, a surgeon may be able to adjust this amount of interference differently about different axes depending upon how many adjustment members 76 are provided. In the embodiments illustrated, there are four total adjustment members 76, disposed approximately 90 degrees apart from one another. More or fewer adjustment members 76 may be provided. Also, in one embodiment, one of the adjustment members 76 is substantially aligned with the orientation in which a longitudinal member 15 lies. For example, in the embodiment shown, one adjustment member 76 is substantially parallel to the seating surface 24. In one embodiment, an adjustment member 76 is substantially transverse to this seating surface. In the embodiment shown, the adjustment members 76 are setscrews that may be screwed in to create a compressive force H that is shown in FIG. 17. In another embodiment, the adjustment member 76 may be a pin. The compressive force H may create an increased amount of interference that also creates more resistance to motion.

Figure 18:
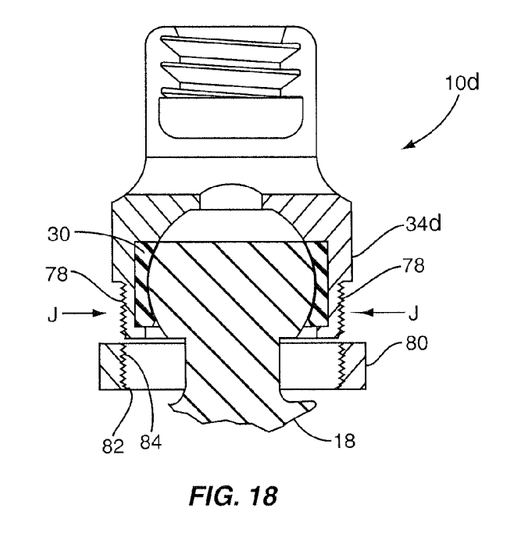
FIG. 18 is a side section view of an assembled pivoting head with an anchor member and wear member constrained therein according to one embodiment.

FIG. 18 shows an alternative embodiment of the pivoting head 10d that includes a threaded region 78 disposed towards a bottom of the base portion 34d. An adjustment member 80 having substantially matching threads 84 is threaded onto the threads 78 on the base portion 34d and rotated until the desired resistance to motion is obtained. This procedure may be performed intra-operatively. In one embodiment, the threads 78, 84 are tapered threads to create an increasing amount of inward compression J and corresponding interference. In one embodiment, a lower opening 82 of the adjustment member 80 is smaller than a width of the threaded portion 78 of the base portion 34d. Consequently, the more the adjustment member 80 is threaded onto the base portion 34d, the base portion 34d is compressed an increasing amount.

Figure 19:
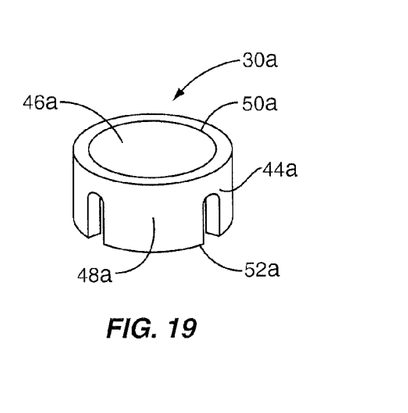
FIG. 19 is a perspective view of a wear member for use with a pivoting head according to one embodiment.

FIG. 19 shows an alternative embodiment of the wear member 30a that may be used in one or more embodiments disclosed herein. The wear member 30a also includes a series of gaps 48a as with the previous embodiment shown in FIG. 6. However, gaps 48a do not extend from the bottom surface 52a to the top surface 50a. In this embodiment, the top surface 50a of the wear member 30a is substantially continuous. In one embodiment, the wear member 30a comprises four gaps 48a separated by approximately 90 degrees. In other embodiments, more or fewer numbers of gaps 48a are used. Since the gaps 48a originate at the bottom surface 52a of the wear member 30a, inward deflection of the wear member 30a, particularly near the bottom surface 52a, is possible. This feature may be appropriate for one or more embodiments where inward deflection of the wear member 30a is used to create a desired resistance to motion.

Figure 20:
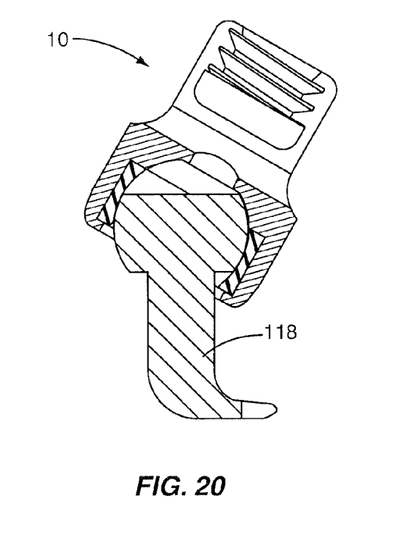
FIG. 20 is a side section view of an assembled pivoting head with an anchor member and wear member constrained therein according to one embodiment.
Figure 21:
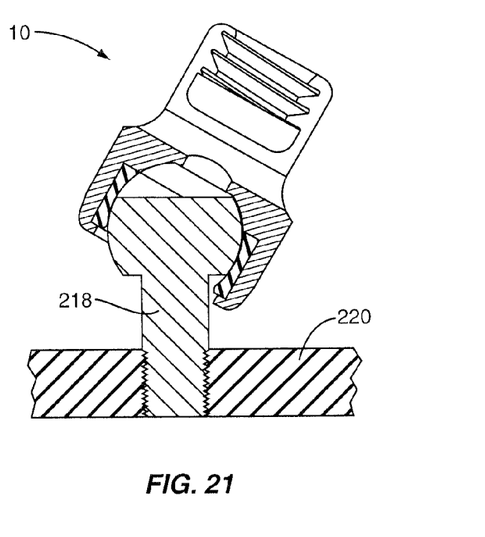
FIG. 21 is a side section view of an assembled pivoting head with an anchor member and wear member constrained therein according to one embodiment.

Embodiments described above have contemplated an anchor member 18 that comprises threads for insertion into a vertebral member V. Certainly, the pivoting head 10 may be incorporated on other types of bone screws. For example, different types of screws may be used to attach longitudinal members 15 to the sacrum S or to other parts of a vertebral member V. These include, for example, anterior and lateral portions of a vertebral body. In other embodiments, such as those shown in FIGS. 20 and 21, the pivoting head 10 may be implemented on other types of anchoring members. For example, FIG. 20 shows a pivoting head 10 incorporated onto a hook-type anchor member 118. In another embodiment shown in FIG. 21, the pivoting head 10 is incorporated onto another type of threaded anchor member 218 that is inserted into a plate 220 instead of a bony member.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. For example, embodiments described above have contemplated a pivoting head 10 having a substantially U-shaped recess in which to hold a longitudinal member 15. Certainly other types of configurations may incorporate the articulation mechanism 40 described herein. For example, alternative embodiments of the pivoting head may have circular apertures, C-shaped clamps, and multi-piece clamps as are known to secure a longitudinal member. The present embodiments are, therefore, to be considered in all respects as illustrative and not restrictive, and all changes coming within the meaning and equivalency range of the appended claims are intended to be embraced therein.

What is claimed is:

1. A method of assembling a vertebral anchor to a body shaped to receive a longitudinal member, the method comprising the steps of:
   inserting a wear member and a head of an anchor into a cavity through an inlet in a first end of a body, the first end of the body having a continuous outer side surface that is free of any gaps, the wear member including an annular body with a gap in a sidewall, the wear member having a uniform height between a top surface and a bottom surface of the wear member, the body further including a second end with a channel to receive the longitudinal member;
   deforming the first end of the body and reducing a width of the inlet measured perpendicular to a longitudinal axis of the body and capturing the wear member and the head in the cavity, wherein deforming the first end of the body and reducing the width of the inlet includes moving the distal end to extend under an outer end of the wear member, the outer end of the wear member facing away from the channel; and
   compressing the wear member against the head of the anchor and decreasing a size of the gap in the wear member and increasing an amount of interference between the wear member and the head.

2. The method of claim 1 further comprising moving the wear member along the longitudinal axis of the body after deforming the first end of the body.

3. The method of claim 1 wherein compressing the wear member against the head of the anchor occurs while deforming the first end of the body and reducing the width of the inlet.

4. The method of claim 1 wherein compressing the wear member against the head of the anchor includes rotating an adjustment member that extends through a sidewall of the cavity and contacts against the wear member.

5. The method of claim 1 further comprising reducing the width of the inlet to be smaller than the head of the anchor.

6. The method of claim 1 further comprising positioning the head of the anchor into an interior of the wear member when the wear member is positioned within the cavity of the body.

7. The method of claim 1 further comprising bottom loading the head of the anchor into the cavity with a tip of the anchor opposite from the head remaining away from the body.

8. A method of assembling a vertebral anchor to a body shaped to receive a longitudinal member, the method comprising the steps of:
   inserting a wear member and a head of an anchor into a cavity in a first end of a body with the first end having a larger width than the wear member, the first end of the body having a continuous outer side surface that is free of any gaps, the wear member having a uniform height between a top surface and a bottom surface of the wear member, the body further including a channel to receive the longitudinal member;
   adjusting a position of the wear member in the cavity relative to the body and to the head;
   positioning the head of the anchor within an interior of the wear member;
   deforming the first end of the body to a width that is smaller than the wear member and capturing the wear member and the head in the cavity; and
   compressing the wear member against the head of the anchor and adjusting an amount of interference between the wear member and the head.

9. The method of claim 8 wherein inserting the wear member and the head of the anchor into the cavity in the first end of the body includes inserting the wear member and the head of the anchor separately into the cavity.

10. The method of claim 8 further comprising reducing the width of the inlet to be smaller than the head of the anchor.

11. The method of claim 8 further comprising deforming the first end of the body and causing the wear member to compress against the head.

12. The method of claim 8 further comprising compressing the wear member and reducing a size of a gap that extends through a sidewall of the wear member.

13. The method of claim 8 wherein adjusting the body comprises screwing a distal section onto the body and over the end of the wear member.

* * * * *